(12) United States Patent
Algee

(10) Patent No.: US 6,990,378 B1
(45) Date of Patent: Jan. 24, 2006

(54) ABRASION-RESISTANT IMPLANTABLE MEDICAL LEAD AND A METHOD OF FABRICATING SUCH A LEAD

(75) Inventor: Alvin Algee, Creston, CA (US)

(73) Assignee: Pacesetter, Inc., Sylmar, CA (US)

( * ) Notice: Subject to any disclaimer, the term of this patent is extended or adjusted under 35 U.S.C. 154(b) by 87 days.

(21) Appl. No.: 10/676,316

(22) Filed: Sep. 30, 2003

(51) Int. Cl.
*A61N 1/04* (2006.01)

(52) U.S. Cl. .................................................. 607/116

(58) Field of Classification Search ............... 607/116, 607/122; 128/898
See application file for complete search history.

(56) References Cited

U.S. PATENT DOCUMENTS

| | | | |
|---|---|---|---|
| 5,466,252 A | 11/1995 | Soukup et al. ............. | 607/116 |
| 5,628,774 A | 5/1997 | Helland et al. ............. | 607/116 |
| 6,078,839 A | 6/2000 | Carson ........................ | 607/116 |
| 6,253,111 B1 | 6/2001 | Carner ........................ | 607/122 |
| 2002/0016622 A1 * | 2/2002 | Janke et al. ................. | 607/116 |
| 2003/0100937 A1 | 5/2003 | Tsuboi et al. ............... | 607/122 |
| 2004/0267342 A1 * | 12/2004 | Alinder ....................... | 607/122 |
| 2005/0027342 A1 * | 2/2005 | Shoberg et al. ............. | 607/122 |

* cited by examiner

*Primary Examiner*—George Manuel
*Assistant Examiner*—Dana D Greene

(57) ABSTRACT

An implantable medical lead comprises an insulating lead body housing having an outer surface. A thin, flexible membrane surrounds the insulating housing, the membrane having an inner surface confronting the outer surface of the housing. A lubricious interface between the inner surface of the membrane and the outer surface of the housing facilitates movement of the insulating housing relative to the membrane in response to frictional engagement of the membrane with adjacent structure. Also disclosed is a method of fabricating such a lead.

19 Claims, 3 Drawing Sheets

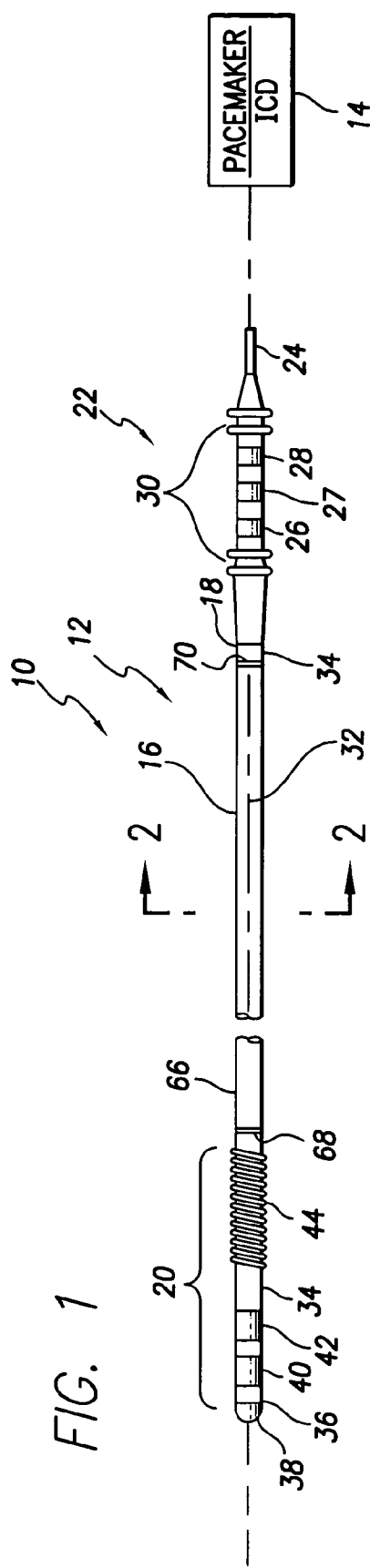
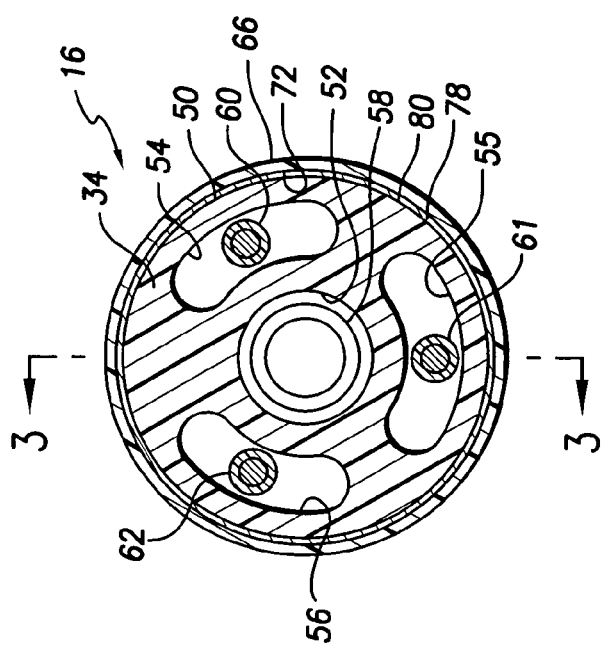

ABRASION-RESISTANT IMPLANTABLE MEDICAL LEAD AND A METHOD OF FABRICATING SUCH A LEAD

FIELD OF THE INVENTION

The present invention relates generally to implantable medical leads for use with implantable medical devices such as pacemakers and/or cardioverter/defibrillators, and more particularly to an implantable medical lead comprising a composite lead body having a lubricious interface that imparts abrasion resistance to the lead body.

BACKGROUND OF THE INVENTION

Various kinds of implantable medical leads for providing stimulation to selected body tissue have become available. For example, an implantable cardiac lead delivers electrical therapy to a patient's heart through one or more electrodes on the distal end of the lead. The electrodes are connected via electrical conductors to a connector assembly on the proximal end of the lead. The connector assembly is in turn coupled to an implantable medical device (IMD) such as a pacemaker or an implantable cardioverter-defibrillator (ICD) or to an IMD combining both pacemaker and ICD functions.

The electrical conductors of an implantable lead are enclosed within an elongated, typically tubular housing made of an insulating material such as silicone rubber or polyurethane. Silicone rubber is known to have superior flexibility and long term biostability but has relatively poor abrasion and tear resistance. Polyurethane, on the other hand, is more resistant to abrasion, cuts and tears but is susceptible to biodegradation and is somewhat stiffer than silicone rubber.

It is desirable that the outer surface of an implantable medical lead have resistance to abrasive wear in the event the lead body rubs against another lead, another implanted device, or the patient's anatomical structure while in use after implantation. Abrasive wear can eventually cause breaks or tears in the lead body's insulating housing and consequent failure of the electrical connection provided by one or more of the electrical conductors. A short circuit, in particular, can potentially damage the circuits of the IMD to an extent requiring its replacement. Insulation abrasion failures account for the largest proportion of all failures in silicone rubber insulated leads.

Thus, there continues to be a need for implantable medical leads, and particularly those with silicone rubber housings, having improved abrasion and tear resistant properties.

SUMMARY

In accordance with one specific, exemplary embodiment of the present invention, there is provided an implantable medical lead comprising a lead body having a proximal end carrying a connector assembly adapted to be received by an implantable medical device, and a distal end carrying at least one electrode. The lead further includes an insulating housing having an outer surface and enclosing at least one electrical conductor connecting the at least one electrode with a terminal contact on the connector assembly. A thin, flexible membrane surrounds the insulating housing, the membrane having an inner surface confronting the outer surface of said housing. A lubricious interface between the inner surface of said membrane and the outer surface of the housing facilitates movement of the insulating housing relative to the membrane in response to frictional engagement of the membrane with adjacent structure. The flexibility of the membrane and the properties of the lubricious interface are such that the membrane will slide over the lead body housing and stretch, wrinkle, twist or wind as the lead body housing moves relative to the patient's body tissue such as the wall of a vein. The relative motion between the membrane and the housing greatly reduces abrasive wear of the lead body. Further, the invention preserves the small outer diameter of the lead, as well as lead flexibility and isodiametric features.

In accordance with another aspect of the invention, the confronting surfaces of the membrane and the housing define between them a sealed space containing the lubricious interface. Further in this regard, the membrane may have a sealed distal end located proximally of the at least one electrode and a sealed proximal end located distally of the connector assembly.

In accordance with one preferred form thereof, the lubricious interface may comprise a biostable, biocompatible, medical grade material selected from the group consisting of silicone oil, silicone gel, silicone foam, silicone grease, PTFE powder, mineral oil, mineral paste and mineral powder. In accordance with another preferred form thereof, the lubricious interface may comprise a lubricious coating on the inner surface of the membrane, on the outer surface of the housing, or on both surfaces.

Pursuant to another aspect of the invention, the membrane may be disposed over the outer surface of the housing in an interference fit, a clearance fit, or an even fit. Preferably, the insulating housing may be fabricated of silicone rubber, while the membrane may comprise a biostable, biocompatible, medical grade, elastic material selected from the group consisting of silicone rubber, polyurethane, polyester, a woven fabric, a knitted fabric, a composite fabric, a memory shaped polymer and a silicone-urethane copolymer.

In accordance with still another specific, exemplary embodiment of the invention, the distal end of the lead body may carry at least two spaced-apart electrodes comprising a distal electrode and a proximal electrode, the mentioned membrane being located between the distal and the proximal electrodes. In this embodiment, the lead further includes a second, thin, flexible membrane surrounding the insulating housing, the second membrane being located between the proximal end of the proximal electrode and the distal end of the connector assembly. The second membrane has an inner surface confronting the outer surface of said housing, and a lubricious interface, preferably in one of the forms described above, between the inner surface of the second membrane and the outer surface of the housing facilitates movement of the insulating housing relative to the second membrane in response to frictional engagement of the second membrane with adjacent structure.

In accordance with another specific, exemplary aspect of the present invention, there is provided a method of fabricating an abrasion-resistant implantable medical lead comprising a distal end carrying at least one electrode electrically connected to a contact on a connector assembly attached to a proximal end of the lead, and an insulating housing having an outer surface. The method comprises the steps of enclosing a portion of the housing in a membrane having a distal end and a proximal end, sealing one of the ends of the membrane to the outer surface of the housing adjacent the at least one electrode or adjacent the connector assembly, injecting a lubricious medium into the space defined between the membrane and the outer surface of the housing, and sealing the other end of the membrane to the outer surface of the housing. Preferably, the membrane comprises a thin, stretchable, tubular structure, and before the second sealing step, the membrane is stretched so that it lies against the outer surface of the housing, the housing and the membrane being dimensioned for an interference fit. Alternatively, the housing and the membrane may be dimensioned for a clearance fit, or for an even fit.

An alternative embodiment of the method of the present invention for fabricating an abrasion-resistant implantable medical lead comprises the steps of enclosing a portion of the lead body housing in a membrane having a distal end and a proximal end, sealing the ends of the membrane to the outer surface of the housing, and injecting a lubricious medium through the membrane into the space defined between the membrane and the outer surface of the housing. If necessary, the portion of the membrane through which the lubricious medium was injected is sealed with, for example, a medical adhesive.

Yet another alternative embodiment of the method of the present invention for fabricating an abrasion-resistant implantable medical lead comprises the steps of providing an insulating housing having an outer surface, enclosing a portion of the housing in a membrane having an inner surface, a distal end and a proximal end, the outer surface of the housing or the inner surface of the membrane or both of those surfaces having a lubricious coating, and attaching the ends of the membrane to the outer surface of the housing.

BRIEF DESCRIPTION OF THE DRAWINGS

The foregoing and other objects, features and advantages of the invention will be evident to those skilled in the art from the detailed description below, taken together with the accompanying drawings, in which:

FIG. 1 is a side view of an implantable cardiac pacing, sensing and cardioverting/defibrillating system, including a lead in accordance with one embodiment of the present invention;

FIG. 2 is a transverse cross section view of the lead shown in FIG. 1 as seen along the line 2—2 in FIG. 1;

DETAILED DESCRIPTION OF THE INVENTION

The following description is of a best mode presently contemplated for practicing the invention. This description is not to be taken in a limiting sense but is made merely for the purpose of describing the general principles of the invention whose scope is defined by the appended claims. Although the invention will be described in the context of implantable cardiac stimulation and sensing leads, it will be evident to those skilled in the art that the invention described herein has broader utility, being applicable to a wide variety of implantable medical leads for stimulating selected body tissue and sensing the electrical activity of such tissue.

Figure 3:
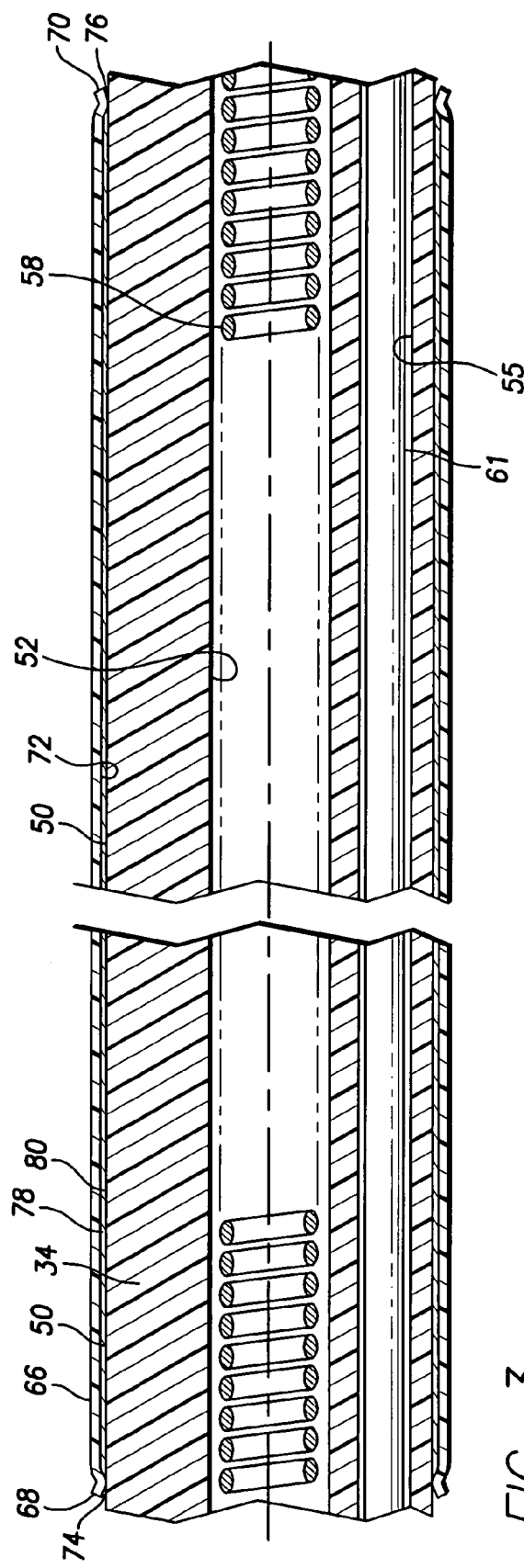
FIG. 3 is an axial cross section view of a portion of the lead shown in FIG. 1 as seen along the line 3—3 in FIG. 2.

By way of example and not limitation, FIGS. 1–3 show an endocardial pacing, sensing and defibrillation system 10 comprising a lead 12 and an implantable medical device (IMD) 14 that may comprise a pacemaker/ICD. The lead 12 includes a lead body 16 having a proximal end 18 and a distal end 20. The lead 12 is illustrated to be of a quadripolar design, but is not intended to be limiting of the invention. The proximal end 18 of the lead 12 incorporates a connector assembly 22 compatible with a standard such as the IS-4 standard for connecting the lead body to the IMD 14. The connector assembly 22 includes a tubular pin terminal contact 24 and ring terminal contacts 26–28 electrically coupled to electrodes along the distal end 20 of the lead body. The connector assembly 22 of the lead is received within a receptacle (not shown) in the IMD 14 containing electrical terminals positioned to engage the contacts 24 and 26–28 on the connector assembly 22. As is well known in the art, to prevent ingress of body fluids into the receptacle, the connector assembly 22 is provided with spaced sets of seals 30. In accordance with standard implantation techniques, a stylet or guide wire (not shown) for delivering and steering the distal end of the lead body during implantation is inserted into a lumen of the lead body through the tubular connector terminal pin 24.

The lead body 16 extends along a central, longitudinal axis 32 and preferably comprises a tubular sheath or housing 34 made of an insulating, biocompatible, biostable polymer, for example, silicone rubber or polyurethane. Although various insulating housing materials are intended to be encompassed by the invention, silicone rubber is often preferred because of its flexibility and long term biostability.

The distal end 20 of the lead body may carry one or more electrodes whose configurations, functions and placement along the length of the distal end will be dictated by the indicated stimulation therapy, the peculiarities of the patient's anatomy, and so forth. The lead body 16 illustrates but one example of the various combinations of stimulating and/or sensing electrodes that may be utilized. More particularly, the distal end 20 of the lead body terminates at a distal extremity 36 incorporating an electrical stimulating and/or sensing tip electrode 38. As is well known in the art, the distal end of the lead body is placed so as to position the surface of the tip electrode 38 in electrical communication with the body tissue to be stimulated and/or sensed.

In conventional fashion, the distal end 20 of the lead body may include passive fixation means (not shown) that may take the form of conventional projecting tines for anchoring the lead body within the right atrium or right ventricle of the heart. Alternatively, the passive fixation or anchoring means may comprise one or more preformed humps, spirals, S-shaped bends, or other configurations manufactured into the distal end 20 of the lead body 16 where the lead is intended for left heart placement within a vessel of the coronary sinus region. The fixation means may also comprise an active fixation mechanism such as a helix. It will be evident to those skilled in the art that any combination of the foregoing fixation or anchoring means may be employed.

The distal end 20 of the lead body may also carry one or more ring electrodes as well as one or more cardioverting/defibrillating coils. In the example under consideration, two ring electrodes 40 and 42 and a single cardioverting/defibrillating coil 44 are included. The ring electrodes 40 and 42 may serve as both tissue-stimulating and sensing electrodes. Other electrode configurations may, of course, be employed pursuant to lead constructions well known in the art. For example, an alternative electrode arrangement may include additional ring stimulation and/or sensing electrodes as well as additional cardioverting and/or defibrillating coils spaced apart along the distal end of the lead body. Thus, as emphasized, FIGS. 1–3 are illustrative only; the distal end of the lead body may carry only pacing and sensing electrodes, only cardioverting/defibrillating electrodes or a combination of pacing, sensing and cardioverting/defibrillating electrodes. Where defibrillating electrodes are included these may be of conventional coil design or, for greater flexibility, they may comprise spaced apart, relatively short metallic rings or they may be made of an electrically conductive polymer or coating. The kind of electrode configuration used will depend upon the particular application and accordingly any electrode configuration known in the art or developed in the future may be utilized. The ring and cardioverting/defibrillating electrodes 40, 42 and 44 shown in the example are electrically connected to the ring terminal contacts 26–28 on the connector assembly 22.

In accordance with one form of the invention, the lead body 16 may be isodiametric, that is, the outside diameter of the lead body may be the same throughout its entire length. By way of example and not limitation, the outside diameter of the lead body 16 may range from about 0.026 inch (2F) to about 0.130 inch (10F). Also, in accordance with well known techniques, the outer surface of the lead body 16 may have a lubricious coating along its length to facilitate its movement through a lead delivery introducer and the patient's vascular system.

The insulating housing 34 may have various cross-sectional configurations. In the example shown, the housing 34 comprises a tubular, multilumen structure having an outer, generally cylindrical surface 50 (FIGS. 2 and 3). More specifically, the lead body housing 34 is a quadrilumen structure defining four axially or longitudinally extending, parallel passages or lumens comprising a central lumen 52 and three outer lumens 54–56 disposed about the central lumen 52. The central lumen 52 may enclose a low friction liner of PTFE, for example (not shown), through which a stylet, guide wire, or inner coil may be passed for delivering and steering the distal of the lead body during implantation thereof. In the example shown, the central lumen 52 contains an electrical coil conductor 58 connecting the tip electrode 38 to the pin terminal contact 24 on the connector assembly 22.

The lumens 54–56 contain insulated electrical conductors 60–62, respectively, that may each be in the form of a multifilar, braided cable typically of MP35N or MP35N/Ag alloy. Alternatively, one or more of the conductors 60–62 may comprise monofilament, non-coiled wires of, for example, nitinol, MP35N, or the like. The cable or wire conductors 60–62 connect the various ring and cardioverting/defibrillating electrodes 40, 42 and 44 on the distal end of the lead body with the associated terminal contacts 26–28 on the proximal connector assembly.

In accordance with one specific, exemplary embodiment of the invention, the lead body housing 34 between the connector assembly 22 and the proximal end of the cardioverting/defibrillating electrode 44 is enclosed within a thin, flexible, stretchable, sleeve-like or tubular, polymer membrane 66. The tubular membrane 66 has a distal end 68 adjacent to the proximal end of the cardioverting/defibrillating electrode 44, a proximal end 70 adjacent to the distal end of the connector assembly 22, and an inner surface 72 confronting the outer surface 50 of the housing 34. The distal end 68 of the tubular membrane is attached to the outer surface 50 of the housing by means of a continuous, fluid-tight, circumferential seal 74 of medical adhesive or a comparable bonding agent. A similar circumferential seal 76 of medical adhesive or comparable bond attaches the proximal end 70 of the membrane to the outer surface of the housing. The confronting inner surface 72 of the membrane and the outer surface 50 of the housing thus define a thin, annular, fluid-tight interface space 78 sealed at its opposite ends. In the embodiment of FIGS. 1–3, the space 78 contains a lubricious interface in the form of a lubricious medium 80.

Without limitation, the following material and dimensional examples are provided:

A. The membrane 66 may be made of any thin, flexible (that is, stretchable), biocompatible, biostable material such as, without limitation, any of the following:
  1. Medical grade elastomeric silicone rubber;
  2. Medical grade elastic polyurethane;
  3. Medical grade elastic polyester;
  4. Woven, knitted, or composite fabrics with controlled stretch;
  5. Flexible plastic memory shaped polymers; and
  6. Silicone-urethane copolymers.

B. The thickness of the membrane 66 in its relaxed state may range from about 0.0005 inch to about 0.005 inch.

C. The lubricious medium 80 contained within the interface space 78 may comprise, without limitation:
  1. A medical grade silicone oil, gel, foam or grease;
  2. A medical grade PTFE powder; or
  3. A hydrocarbon agent such as mineral oil, paste or powder.

D. By way of example only, the volume of the lubricious medium 80 injected into the space 78 may comprise approximately 0.01 cc per linear centimeter of the length of the space 78.

The tubular membrane 66 is slid into place over the housing preferably in an interference fit so that the membrane is stretched longitudinally and circumferentially over the outer surface of the housing 34 when it is installed. For example, the housing may have an outer diameter of 0.060 inch while the membrane may have an inner diameter of 0.058 inch in its unstretched state. Using a medical adhesive or comparable bonding agent, one end 68 or 70 of the tubular membrane 66 is then attached to the outer surface 50 of the housing 34 about the entire circumference of the housing to seal the one end of the membrane at 74 or 76. The lubricious medium 80 is then injected into the interface space 78; the medium will form a thin film within the space 78. The other end 68 or 70 of the membrane is then similarly attached to the outer surface 50 of the housing to completely seal the filled interface space 78. Alternatively, both ends of the membrane 66 may be sealed followed by injection of the medium 80 through the wall of the membrane using a hypodermic needle or comparable expedient. If necessary, the puncture through the membrane may be sealed with medical adhesive. Alternatively, instead of an interference fit between the housing and the membrane, these elements may be dimensioned for a clearance fit or an even fit. By way of example, an appropriate interference fit may be obtained when, prior to assembly of the housing 34 and the membrane 66, the diameter of the outer surface 50 of the housing 34 is greater, for example, by 0.001 inch, than the diameter of the inner surface 72 of the membrane 66 in its unstretched state. A clearance fit may be obtained when prior to assembly the diameter of the housing surface 50 is less, for example, by 0.001 inch than the diameter of the membrane surface 72. An even fit may be obtained when the aforementioned diameters are the same prior to assembly.

Figure 4:
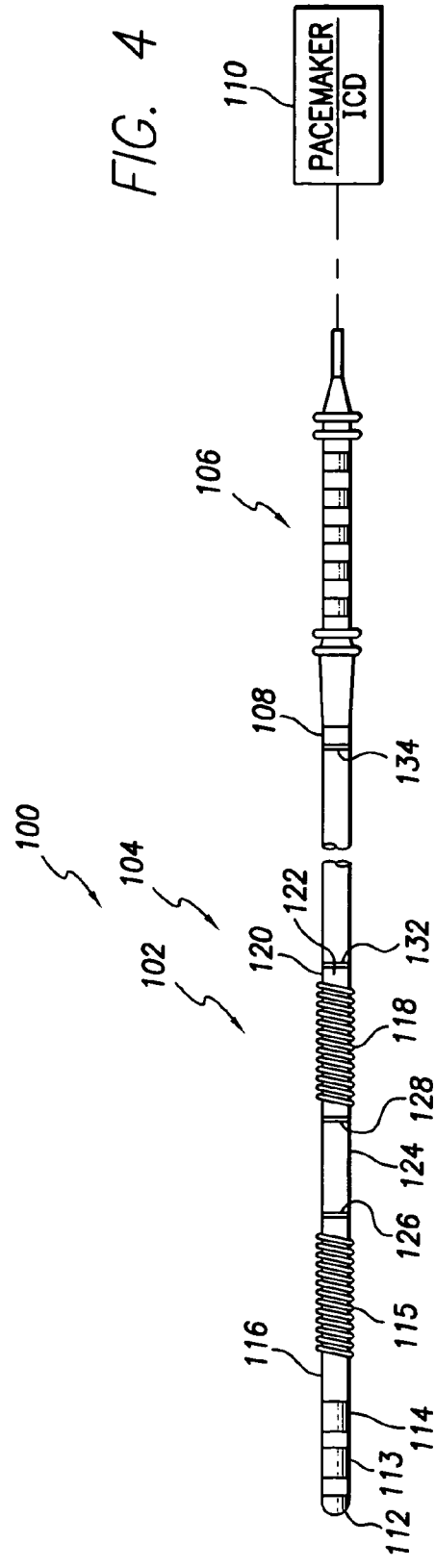
FIG. 4 is a side view of an implantable cardiac pacing, sensing and cardioverting/defibrillating system, including a lead in accordance with an alternative embodiment of the invention.

Turning now to FIG. 4, there is shown an implantable cardiac pacing, sensing and cardioverting/defibrillating system 100 that includes a lead 102 in accordance with an alternative embodiment of the invention. Generally, the description of the lead shown in FIG. 1 is applicable to the alternative embodiment of FIG. 4. Thus, the lead 102 includes a lead body 104 having a connector assembly 106 at a proximal end 108 of the lead body. The connector assembly 106 is adapted to be received by an IMD such as a pacemaker/ICD 110. A plurality of spaced-apart electrodes 112–115 including a cardioverting/defibrillating electrode 115 are disposed along a distal end 116 of the lead body. The cardioverting/defibrillating electrode 115 may be positioned along the distal end of the lead body so as to provide electrical stimulation to, for example, the right ventricle of the heart. In addition to the cardioverting/defibrillating electrode 115, the embodiment of FIG. 4 includes a second cardioverting/defibrillating electrode 118 disposed along the distal end 116 proximally of the first cardioverting/defibrillating electrode 115 and positioned to stimulate, by way of example, the tissue of the superior vena cava (SVC). The lead body 104 includes a polymer, tubular housing 120 of silicone rubber or the like having an outer surface 122.

In accordance with the alternative embodiment of FIG. 4, the portion of the lead body housing 120 between the cardioverting/defibrillating electrodes 115 and 118 is enclosed within a first membrane 124 having the properties already described in connection with the first embodiment. The membrane 124 has a distal end 126 adjacent to the proximal end of the first cardioverting/defibrillating electrode 115 and a proximal end 128 adjacent to the distal end of the second cardioverting/defibrillating electrode 118. The membrane ends 126 and 128 are attached to the outer surface 122 of the lead body housing 120 by means of continuous, fluid tight, circumferential seals of medical adhesive or a comparable bonding agent in the manner already described. The portion of the lead body housing 120 between the proximal end of the second cardioverting/defibrillating electrode 118 and the distal end of the connector assembly 106 is enclosed within a second membrane 130 having the properties already described. The membrane 130 is attached to the outer surface 122 of the lead body housing 120 by means of continuous, fluid tight, circumferential seals at opposed, distal and proximal ends 132 and 134, respectively, of the membrane. As before, the annular, thin, fluid-tight interface spaces between the membranes 124 and 130, on the one hand, and the outer surface 122 of the housing 120, on the other, each contains a lubricious interface in the form of a lubricious medium, all as previously described.

Figure 5:
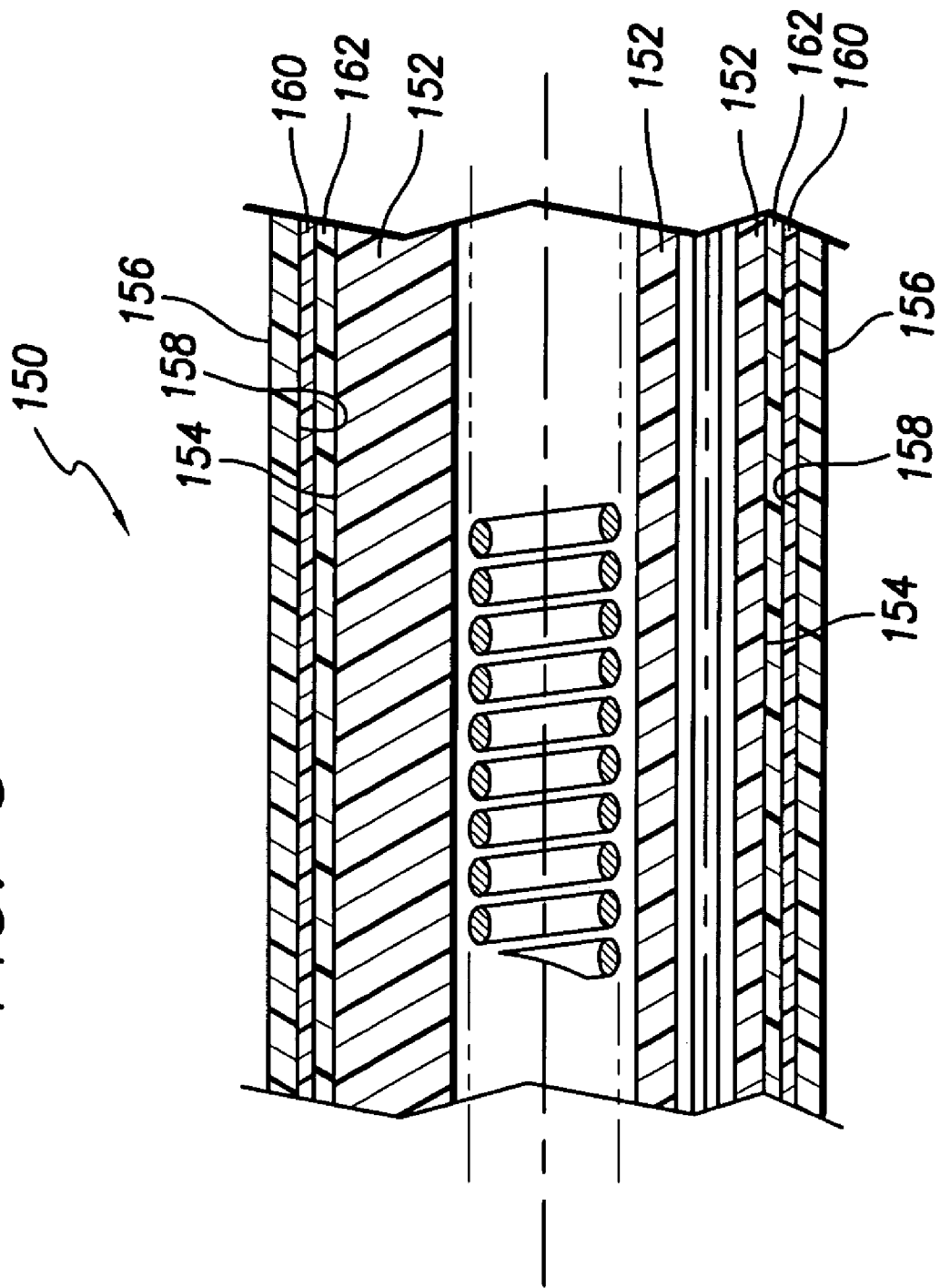
FIG. 5 is an axial cross section view of a portion of a lead in accordance with yet another alternative embodiment of the invention.

In accordance with another specific embodiment of the invention, the lubricious interface between the membrane(s) and the associated lead body housing may comprise, instead of an injectable medium, various surface treatments or surface modifications such as lubricious thin films or coatings. Thus, with reference to FIG. 5, there is shown in axial cross-section a portion of a lead body 150 including, as before, a lead body housing 152 having an outer surface 154. The outer surface 154 of the lead body housing along at least a portion of the length thereof is enclosed within a membrane 156 of the kind previously described. The membrane 156 has an inner surface 158 confronting the outer surface 154 of the lead body housing 152. Disposed between the confronting inner surface 158 of the membrane 156 and the outer surface 154 of the housing 152 is a lubricious interface that, in accordance with the specific, exemplary embodiment of FIG. 5, comprises a lubricious film or coating 160 on the inner surface 158 of the membrane 156 and a lubricious film or coating 162 on the outer surface 154 of the lead body housing. It will be evident that instead of providing a lubricious film or coating on each of the two surfaces 154 and 158, such a film or coating may be provided on only one of the two surfaces. The lubricious film or coating 160, 162 may take the form of any of the well known lubricious films or coatings that are presently applied to the outer surface of implantable leads, for example, the molecular coatings on cardiac leads sold by St. Jude Medical, Inc., under the registered trademark, "FAST-PASS". It will be evident that the embodiment of FIG. 5 is applicable to the single membrane lead body structure of FIGS. 1–3 as well as to the multiple membrane structure of FIG. 4.

The flexibility of the membrane(s) and the properties of the lubricious interface of the various embodiments disclosed herein are such that the membrane(s) will slide over the lead body housing and stretch, wrinkle, twist or wind as the lead body housing moves relative to the patient's body tissue such as the wall of a vein. The relative motion between the membrane(s) and the housing greatly reduces abrasive wear of the lead body. Further, the invention preserves the small outer diameter of the lead, as well as lead flexibility and isodiametric features. Moreover, it will be apparent that the invention is applicable to all implantable medical leads, including both endocardial and epicardial cardiac leads.

While several illustrative embodiments of the invention have been shown and described, numerous variations and alternative embodiments will occur to those skilled in the art. Such variations and alternative embodiments are contemplated, and can be made without departing from the spirit and scope of the invention as defined in the appended claims.

What is claimed is:
1. An implantable medical lead comprising:
a lead body having a proximal end carrying a connector assembly adapted to be received by an implantable medical device and a distal end, and at least one electrode for patient stimulation connected to said lead body; said lead body further comprising:
an insulating housing defining an outer surface and enclosing at least one electrical conductor connecting said at least one electrode with said connector assembly;
a flexible membrane surrounding said insulating housing, said membrane inner surface confronting said outer surface of said insulating housing;
a distal circumferential seal attaching a distal portion of said membrane to said outer surface of said insulating housing;
a proximal circumferential seal attaching a proximal portion of said membrane to said outer surface of said insulating housing;
wherein said distal circumferential seal and said proximal circumferential seal define a sealed space between said inner surface of said membrane and said outer surface of said insulating housing; and
a lubricious medium disposed within said sealed space;
wherein flexibility of the membrane and the properties of the lubricious medium enable said membrane to slide over said insulating housing and deform as said insulating housing moves relative to a patient's body tissue; and
wherein relative motion between said membrane and said insulating housing reduces abrasive wear of said lead body.
2. The lead of claim 1 in which:
said distal circumferential seal is located proximally of said at least one electrode and said proximal circumferential seal is located distally of the connector assembly.

3. The lead of claim 1 in which:
said lubricious medium comprises a biostable, biocompatible, medical grade material selected from the group consisting of silicone oil, silicone gel, silicone foam, silicone grease, PTFE powder, mineral oil, mineral paste and mineral powder.

4. The lead of claim 1 in which:
the volume of said lubricious medium contained in said sealed space comprises approximately 0.01 cc per linear cm of the length of said sealed space.

5. The lead of claim 1 in which:
said lubricious medium comprises a lubricious coating on at least one of said surfaces.

6. The lead of claim 1 in which:
the membrane has a tubular configuration.

7. The lead of claim 6 in which:
the membrane is disposed over said outer surface of said housing in an interference fit.

8. The lead of claim 6 in which:
the membrane is disposed over said outer surface of said housing in a clearance fit.

9. The lead of claim 6 in which:
the membrane is disposed over said outer surface of said housing in an even fit.

10. The lead of claim 1 in which:
the insulating housing is fabricated of silicone rubber.

11. The lead of claim 1 in which:
the membrane comprises a biostable, biocompatible, medical grade, elastic material selected from the group consisting of silicone rubber, polyurethane, polyester, a woven fabric, a knitted fabric, a composite fabric, a memory shaped polymer and a silicone-urethane copolymer.

12. The lead of claim 1 in which:
said distal end of the lead body carries at least two, spaced-apart electrodes comprising a distal electrode and a proximal electrode;
said membrane is located between said distal and proximal electrodes; and
wherein the lead further includes:

a second, thin, flexible membrane surrounding said insulating housing, said second membrane being located between the proximal end of the proximal electrode and the distal end of the connector assembly, the second membrane further having an inner surface confronting the outer surface of said housing; and a lubricious medium between said inner surface of said second membrane and said outer surface of said housing, said lubricious medium facilitating movement of said insulating housing relative to the second membrane in response to frictional engagement of the second membrane with adjacent structure.

13. The lead of claim 12 in which:
each of said lubricious media comprises a biostable, biocompatible, medical grade material selected from the group consisting of silicone oil, silicone gel, silicone foam, silicone grease, PTFE powder, mineral oil, mineral paste and mineral powder.

14. The lead of claim 12 in which:
each of said lubricious media comprises a lubricious coating on at least one of said surfaces.

15. The lead of claim 1 in which:
the lubricious medium is a fluid, and the confronting surfaces define between them a fluid-tight interface space sealed at opposite ends to contain the fluid.

16. The lead of claim 1 further comprising:
a fluid-tight chamber having a first surface defined by the outer surface of the insulating chamber and a second surface defined by the inner surface of the membrane.

17. The lead of claim 16 in which:
the lubricious medium is injectable into the fluid-tight chamber.

18. The lead of claim 1 in which:
membrane deformation comprises wrinkle, twist or wind.

19. The lead of claim 1 in which:
said distal circumferential seal and said proximal circumferential seal comprise a medical adhesive.

* * * * *